(12) United States Patent  
Salda et al.

(10) Patent No.: US 9,302,024 B2  
(45) Date of Patent: Apr. 5, 2016

(54) MACHINE FOR NEUTRALIZING THE BACTERIAL CONTENT OF HOSPITAL WASTE OR OTHER SPECIAL WASTE, SO AS TO BE ABLE TO DISPOSE OF IT AS WASTE SIMILAR TO ORDINARY SOLID WASTE

(75) Inventors: Luciano Salda, Vignola (IT); Angelo Cappi, Vignola (IT); Cristina Leonelli, Savignano Sul Panaro (IT); Paolo Veronesi, Modena (IT)

(73) Assignee: C.M.S. S.P.A., Province of Modena (IT)

( * ) Notice: Subject to any disclaimer, the term of this patent is extended or adjusted under 35 U.S.C. 154(b) by 839 days.

(21) Appl. No.: 13/520,249

(22) PCT Filed: Dec. 29, 2010

(86) PCT No.: PCT/EP2010/070876  
§ 371 (c)(1),  
(2), (4) Date: Jul. 2, 2012

(87) PCT Pub. No.: WO2011/083067  
PCT Pub. Date: Jul. 14, 2011

(65) Prior Publication Data  
US 2012/0282152 A1 Nov. 8, 2012

(30) Foreign Application Priority Data  
Jan. 7, 2010 (IT) .............................. BO2010A0003

(51) Int. Cl.
| | |
|---|---|
| *A61L 11/00* | (2006.01) |
| *A61L 2/12* | (2006.01) |
| *A61L 2/24* | (2006.01) |
| *H05B 6/80* | (2006.01) |

(52) U.S. Cl.  
CPC . *A61L 11/00* (2013.01); *A61L 2/12* (2013.01); *A61L 2/24* (2013.01); *H05B 6/80* (2013.01); *H05B 2206/045* (2013.01)

(58) Field of Classification Search  
CPC .............. A61L 2/12; A61L 2/24; A61L 11/00  
See application file for complete search history.

(56) References Cited

U.S. PATENT DOCUMENTS 6,524,539 B1 * 2/2003 Katschnig et al. ....... 422/186.07  
2006/0120914 A1 6/2006 Salda

FOREIGN PATENT DOCUMENTS

WO WO 2009/015688 2/2009  
WO WO 2010/040690 4/2010

OTHER PUBLICATIONS

International Search Report for PCT/EP2010/070876 Dated Feb. 28, 2011.  
Written Opinion of the International Searching Authority for PCT/EP2010/070876 Dated Feb. 28, 2011.

* cited by examiner

*Primary Examiner* — Timothy Cleveland  
(74) *Attorney, Agent, or Firm* — Marvin Petry; Stites & Harbison PLLC

(57) ABSTRACT

The microwave sterilization chamber (10) is made in the shape of a downwardly open bell which can be sealed by a base structure (6, 19, 20) which carries means (5) for gripping and rotating the canister (1) filled with waste, which can be moved by suitable means from a low position for the filling and discharge of the canister (1) to a raised position for the closure of said chamber and for the insertion of the full canister (1) into the chamber, each canister being provided with means by which it can be removably supported by said means of gripping and rotating the sterilization chamber (10), and can be gripped by the manipulating means (SM) which transfer said canister between the different operating stations of the machine.

7 Claims, 5 Drawing Sheets

MACHINE FOR NEUTRALIZING THE BACTERIAL CONTENT OF HOSPITAL WASTE OR OTHER SPECIAL WASTE, SO AS TO BE ABLE TO DISPOSE OF IT AS WASTE SIMILAR TO ORDINARY SOLID WASTE

In the course of the construction of the equipment and the application of the method described in the prior art document WO 2010/040690 A1, certain improvements which make the invention industrially applicable were identified and are described herein. In order to give a clear picture of the objects of the invention, it is worth mentioning that, according to the method described in the cited prior art, a) the waste, having been suitably shredded and moistened, is placed in microwave-permeable cylindrical canisters of the appropriate capacity, which are placed in composite treatment chambers which are pressure-resistant, shielded externally and provided with a plurality of suitable offset apertures distributed at least over the height of each chamber, these apertures being connected to corresponding waveguides leading from microwave generators; b) when filled, each said composite chamber is sealed off from the exterior and is prepared for the sterilization of the corresponding waste within it at the correct moisture, pressure and temperature levels, using appropriate cycle times, with the execution of a preliminary step of internal depressurization of each said composite chamber if required; c) the microwave generators are switched on and the canisters holding the accumulations of waste in said treatment chambers are made to rotate about their axes with respect to the microwave radiation apertures, so as to achieve the uniformly distributed sterilization of said various accumulations of waste, even if statically located magnetrons of limited power are used; d) on completion of the waste sterilization cycle, the treatment chambers are brought to atmospheric pressure and are opened for the discharge of the sterilized waste which can then be disposed of as waste similar to ordinary solid waste, and for the start of a new operating cycle.

The invention relates to equipment which substantially makes use of this method, but in which, unlike the example described in the preceding patent, the waste canisters are bodies which can be moved by the sterilization chambers and are provided with baseplates or other interfaces having a suitable shape for manipulation by an appropriate structure of filling and discharging said composite chambers, which in this case are constructed in the form of downwardly open cylinders sealed below by a vertically movable base structure which is provided with a small rotating platform with a clamp for gripping said base of each canister. When the canister filled with waste has been placed on said platform, said base structure of each sterilization chamber is raised and sealed and its platform is activated for the rotation of the full canister supported by it, and the waste is irradiated by the various beams of microwaves. When the waste has been sterilized and the treatment chamber has been depressurized, the base structure of the chamber is lowered, and the canister of treated waste is picked up by the manipulating structure which removes it, rotates it downwards, causes it to interact with an emptying and cleaning structure, and then returns it to the vertical, upwardly open position, places it in a station for filling with new waste and finally reinserts it into a sterilization chamber for the execution of a new operating cycle. These and other characteristics of the invention will be made clear by the following description of a preferred embodiment of the invention, illustrated purely by way of non-limiting example in the figures, in which:

Figure 1:
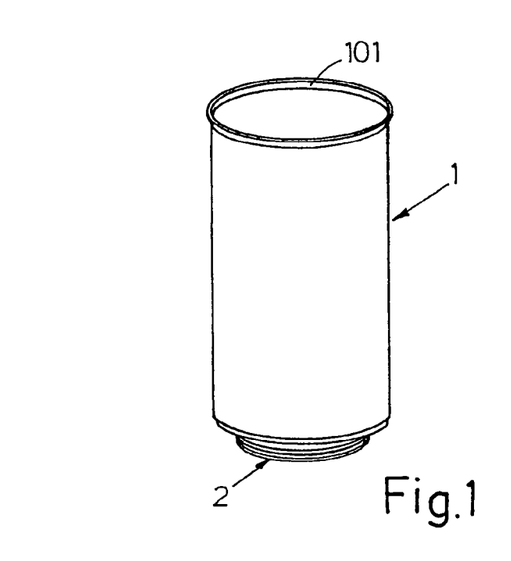
FIG. 1 is a perspective view of one of the canisters for containing the waste to be treated.
Figure 2:
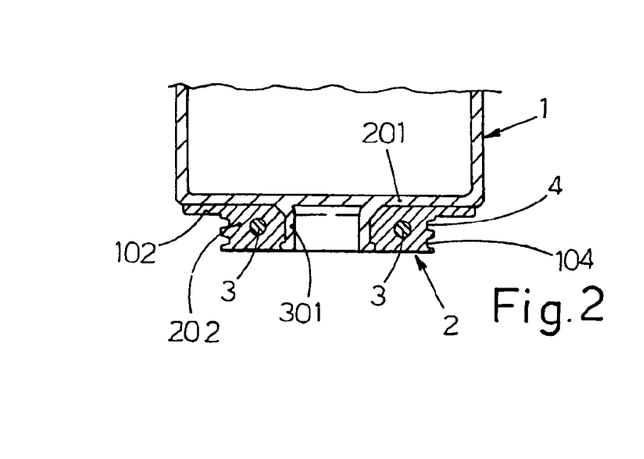
FIG. 2 shows the lower part of the canister of FIG. 1 in diametric cross section, with the baseplate which is to be gripped by the manipulating structure and the rotating structure.

FIGS. 1 and 2 show that the waste to be treated is placed in cylindrical canisters 1 having a round cross section, with a suitable capacity, of about 5-6 liters for example, each canister having its upper edge 101 suitably flared and having a base 201 which is, for example, provided with an external axial stem 301 with an anti-slip outer profile of any kind for clamping and locking between the two parts with a diametric division which make up each baseplate 2, these parts being made from a suitable heat-resistant material and joined together by transverse tightening screws 3. The canister 1 can be made from any microwave-permeable heat-resistant material such as Pyrex® (a low-thermal-expansion borosilicate glass). The baseplate 2 is substantially mushroom-shaped and its flat head 102 bears at least on the base of the canister 1, while the stem 202 of said base is characterized in that it has at least two annular grooves 4 and 104, of trapezoidal profile for example, at different heights, the upper groove 4 being designed to be engaged by the jaws of the aforesaid manipulating clamps, while the lower groove 104 is engaged, for example when the canister is at a sterilization station of the machine in question, by at least three jaws 105 (FIGS. 4 and 5) of a self-centring clamp 5 with a vertical axis (see below), mounted on a carriage 6 which can slide on vertical guide and slider units 7 and 8, and which is connected to the rod of a pair of vertical double-acting hydraulic cylinder and piston units 9, 9', whose bodies are supported by brackets 72 fixed to the frame of the machine, by means of which said carriage 6 can be moved from the low position shown in FIG. 4, in which said clamp 5 receives the canister 1 filled with waste from the aforesaid manipulating means, to the raised position shown in FIG. 5, in which the canister 1 is inserted into the static microwave treatment sterilization chamber 10, which in this case is made in the form of a downwardly open cylinder. The sterilization chamber 10 is formed by a strong tubular sleeve 110, made for example from Teflon® (a synthetic fluoropolymer tetrafluoroethylene) or other microwave transparent material, enclosed by a metal shield 510, the whole assembly being sealed at the top by a lid 210 and being provided at its base, with the interposition of a seal, with a flange 310 which is secured to said lid to form a stack by means of a suitable number of rods 410 distributed equally around the assembly 110, 510. On spacers 11 fixed with screws to the cover 210 there are fixed the two shells of a casing 12 (see also FIG. 3) which covers the lid and the outer lateral surface of the chamber 10 and which has the thermal insulation material fitted within it, the casing 12 also being capable of being constructed and used to serve as an additional microwave shield. Valve means 13, sensors 14, and all the means required to control the operation of the chamber 10, according to the procedures described in the preceding patent application cited in the preamble, or in any other useful and safe way, project from the upper part of the sterilization chamber. Screws or studs 111 pass through the spacers 11, are fixed to the lid 210 of the chamber 10 and have a length such that they project by a suitable amount from the casing 12 to enable them to be secured and fixed by corresponding bolts to composite supports 16 (FIGS. 4 and 8) fixed to and projecting from the frame 42 of the machine.

Figures 3, 6:
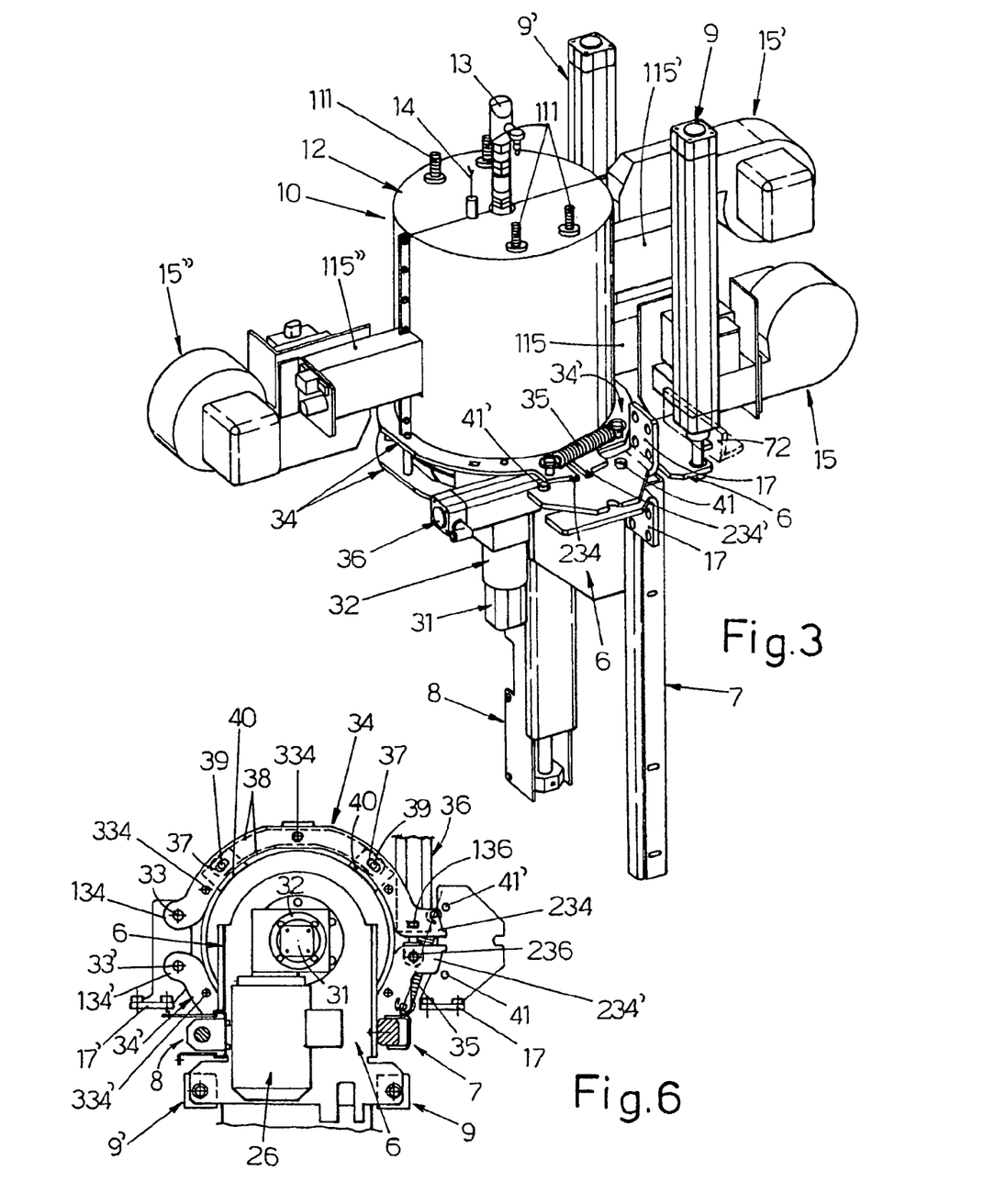
FIG. 3 is a perspective view of one of the sterilization stations for the waste placed in a canister as shown in the preceding figures, in the sealed condition for operation.
FIG. 6 is a plan view from below of the sterilization chamber of the station as shown in FIGS. 3 to 5.

FIG. 3 shows that, as stated in the said prior patent application, the chamber 10 in question is also provided with waveguides 115, 115', 115" which pass through the casing 12, one end of each waveguide being connected to a corresponding aperture (not visible in the drawings) formed in the shield 510, while its outer end is connected to a corresponding microwave source 15, 15', 15" comprising a magnetron of suitable power and corresponding service elements. The microwave injection circuits and said apertures are such that there is sufficiently uniform and/or distributed radiation of the various corresponding regions over the height of the sterilization chamber 10, these regions being suitably offset from each other to avoid the known problems of wave reflection.

Figures 4, 7:
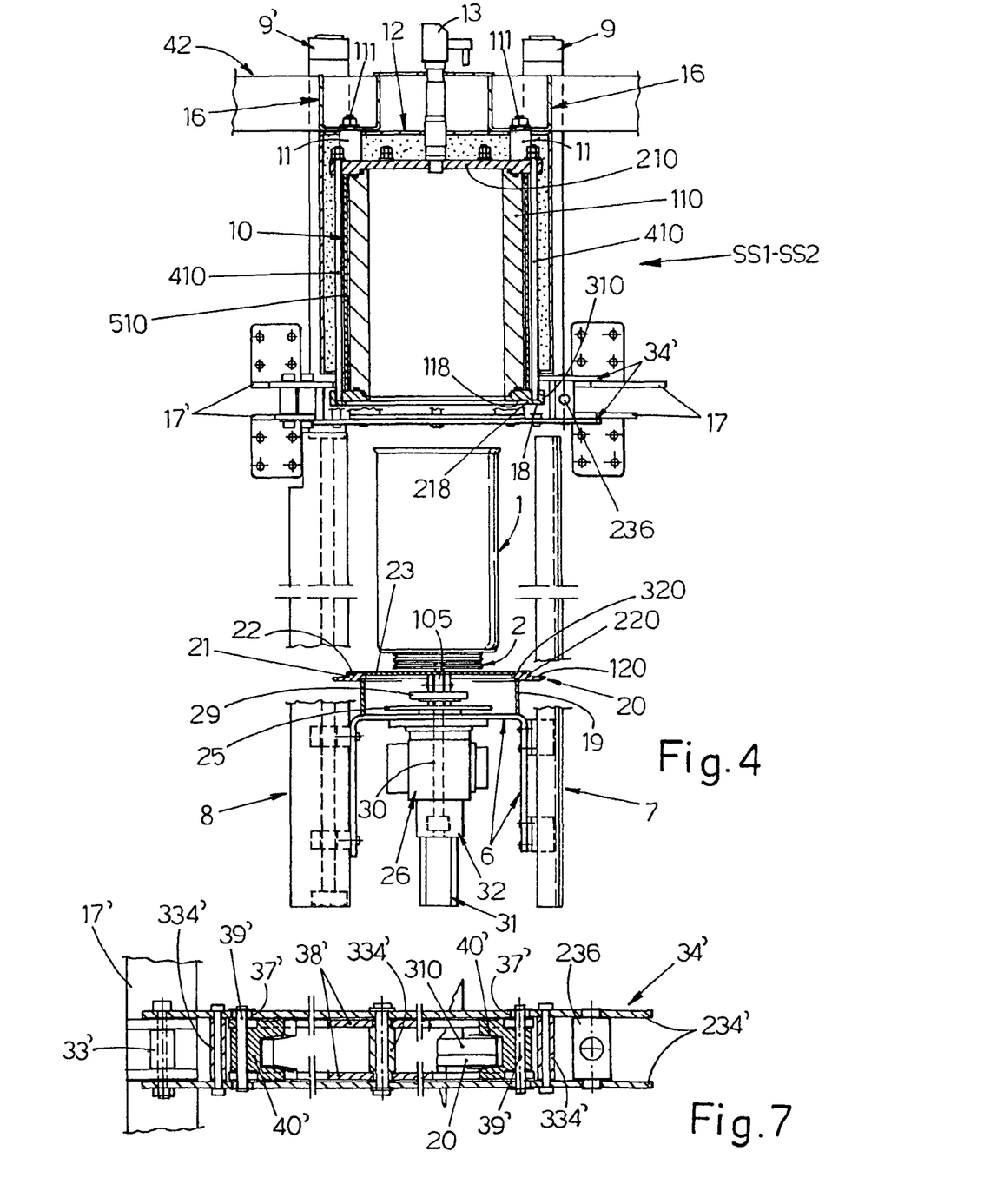
FIG. 4 is a front view of the station of FIG. 3, with parts shown in cross section and in the open condition.
FIG. 7 is a view in vertical longitudinal section of one of the jaws of the collar clamp which seals the bottom of each sterilization chamber as shown in the preceding figures.
Figure 5:
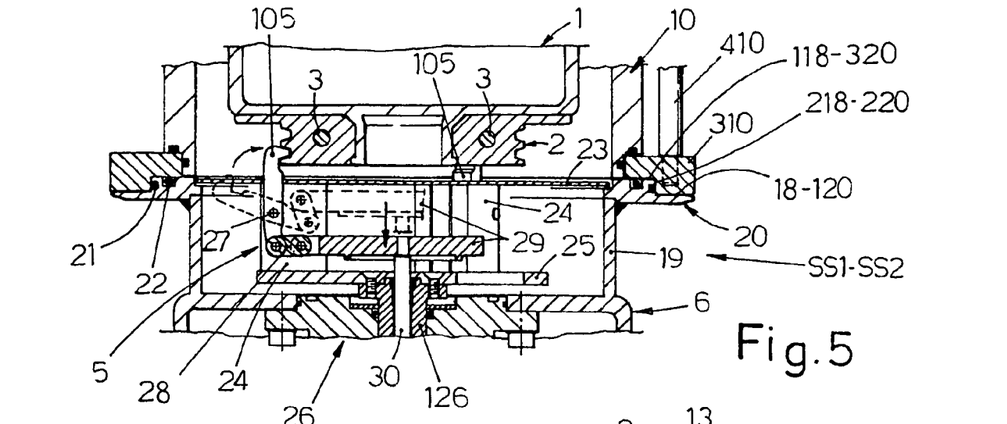
FIG. 5 is an enlarged view, showing further details and with parts in cross section, of the lower part of the sterilization chamber sealed as shown in FIG. 3.

FIGS. 4 and 5 show that the flange 310 imparts a Z-shaped profile to the lower aperture of the sterilization chamber 10, with an outer horizontal bearing surface 18, an inner horizontal bearing surface 118 suitably raised above the former element, and a riser 218 which connects said two bearing surfaces, this riser having a vertical or slightly inclined generatrix which forms a slightly conical and downwardly diverging surface 218. As shown in FIGS. 4, 5 and 6, the carriage 6 is formed by an inverted U-shaped structure, connected by its sides to said guide and slider units 7 and 8, and having a horizontal upper wall carrying, with a lateral seal, a fixed small cylindrical sleeve with a vertical axis 19, on the upper edge of which is fixed with a seal a flange 20 whose upper part has a Z-shaped profile complementary to that of said lower flange 310 of the sterilization chamber 10, such that, when the carriage 6 is raised as shown in FIG. 5, the portion 120 of the flange 20 bears on the lower bearing surface 18 of the flange 310, while its corresponding annular seals 21 and 22, provided on the riser 220 and on the upper bearing surface 320 respectively, bear on the riser 218 and on the inner front bearing surface 118 of said flange 310 respectively with a lateral and frontal seal. The movable flange 20 has a stepped inner profile on which the perimetric edge of a plate 23, with a conjugate profile and with sufficient clearance, is located, the waste canister 1 being positioned and centred above this plate when the carriage 6 is in the low position shown in FIG. 4, the plate also being provided with radial slits through which the jaws 105 of the self-centring clamp 5 pass, these jaws initially being in the low retracted position shown in broken lines in FIG. 5 and being raised on command to grip the baseplate 2 of the canister 1, by engaging with corresponding portions of its lower groove 104. The plate 23 is supported by means of spacers 24 rising from a lower plate 25 fixed to the end flange of the output shaft of a geared motor 26 which in turn is fixed by its casing, in a sealed way, in an aperture of the upper part of the carriage 6, the whole assembly being such that the necessary axial rotation is transmitted to the plate 23 and to the canister 1. As shown in the detailed view of FIG. 5, the jaws 105 of the clamp 5 are pivoted at 27 on pairs of the said spacers 24 and their lower ends are connected by means of links 28 to an operating plate 29 which, by its appropriate downward and upward travel, creates, respectively, the necessary self-centring closing and opening movements of the jaws of the clamp 5, as shown in solid lines and in broken lines respectively in FIG. 5. For this vertical movement, the operating plate 29 is fixed to the upper end of a rod 30 which passes with sufficient clearance and with a lateral seal through an axial cavity of the shaft 126, and which, as shown in FIGS. 3 to 6, emerges from the other end of this shaft for connection to a cylinder and piston unit 31, with the interposition of a freewheel device 32. The cylinders 9, 9' for raising and lowering the carriage 6 have the function of inserting the canister 1, in the raising phase, into the sterilization chamber 10 and coupling the movable flange 20 to the lower flange 310 of the chamber, but they do not have the function of resisting the high pressures which are developed in the chamber during the sterilization of the waste, since this function is performed by other means which will now be described with reference to FIGS. 3, 4, 6 and 7. Pairs of supports 17, 17' (FIGS. 3-6 and 8), fixed to uprights 142 of the machine frame 42, are provided in two diametrically opposed areas of the flange 310 and at a short distance from the flange. On the supports 17' there are pivoted at 33, 33' the slightly outwardly curved ends 134, 134' of jaws formed by pairs of plates 34, 34' which in plan view are shaped in the form of a sector of a circle with an amplitude of slightly less than 180°, the opposite ends 234, 234' of the jaws being oriented towards the outside and being pressed against each other by at least one resilient means 35 fixed to these jaws, while the body of a hydraulic cylinder and piston unit 36 is pivoted at 136 on the end 234 of the jaw 34, the rod of this unit being pivoted at 236 on the opposing end 234' of the jaw 34'. Said pairs of plates forming the curved jaws 34, 34' are interconnected by crosspieces 334, 334' spaced at an angular interval of 90°, the intermediate cross-piece being pivoted on the middle of a corresponding rocker arm 38, 38' which is also formed by a pair of parallel plates (FIGS. 6 and 7), and which resembles a sector of a circle in plan view and has an angular amplitude of approximately ninety degrees. At the ends of these rocker arms there are pivoted, by means of pins 39, 39', blocks 40, 40' resembling sectors of circles in plan view and having a substantially Y-shaped cross section, each block having a groove with the profile of an isosceles trapezium facing towards the sterilization chamber 10, the outer longer base and the inner shorter base of the trapezium having dimensions in elevation which are, respectively, greater and smaller than the sum of the thicknesses of the flange 310 and of the part 120 which bears together with this flange on the flange 20. As shown in the details of FIGS. 6 and 7, the blocks 40, 40' have a sufficient degree of freedom in their oscillation on the corresponding pins 39, 39' before coming into contact with the plates of the corresponding supporting rocker arms 38, 38', and the ends of the pins 39, 39' pass through slots 37, 37' provided on the pairs of plates forming the jaws 34, 34', in such a way that the rocker arms have sufficient freedom of oscillation about their median fulcrum 334, 334'. The curved jaws 34, 34', together with the corresponding pairs of blocks 40, 40', form a collar clamp which encloses the assembly formed by the lower flange 310 of the sterilization chamber and by the underlying flange 20 which is raised against it, and the collar clamp has the function of interacting in a floating centripetal way with the stack formed by said flanges 310, 20, thus being adapted precisely to their round shape and providing the necessary axial thrust to keep them closed, in opposition to the high operating pressures developed in the chamber 10 during the sterilization of the waste. Before the canister 1 is inserted into the chamber 10, while the carriage 6 is still in the low position shown in FIG. 4, the rod of the cylinder 36 is extended so as to move the jaws 34, 34' away from each other in opposition to the action of the spring 35, until the ends 234, 234' are brought to bear with their projecting tips on stops 41, 41' fixed to the supports 17 (FIGS. 3 and 6). In this condition, both the jaws 34, 34' and the blocks 40, 40' are retracted and are suitably distant from the lower flange 310 of the sterilization chamber 10, in order not to interfere with the flange 20 associated with the carriage 6 when the latter is raised to insert the canister 1 into the chamber 10. On completion of insertion, the cylinder 36 is actuated to retract its rod and to close the jaws 34, 34', with the assistance of the spring 35, the corresponding blocks 40, 40' being fitted in a floating centripetal way onto the perimeter of the assembly of flanges 310 and 20, as shown in FIGS. 6 and 7, in such a way that the interaction of the inclined planes of the grooves of the blocks on the upper and lower edges of the assembly of said flanges 310 and 20 causes the assembly to be closed and kept in this closed condition with a minimal force exerted by the cylinder 36. The inclined planes of the grooves of the blocks 40, 40' have the function of substantially reducing the force directed towards the cylinder 36, since this force is proportional to the sine of the angle of the inclined planes of said trapezoidal grooves of the blocks.

Figure 8:
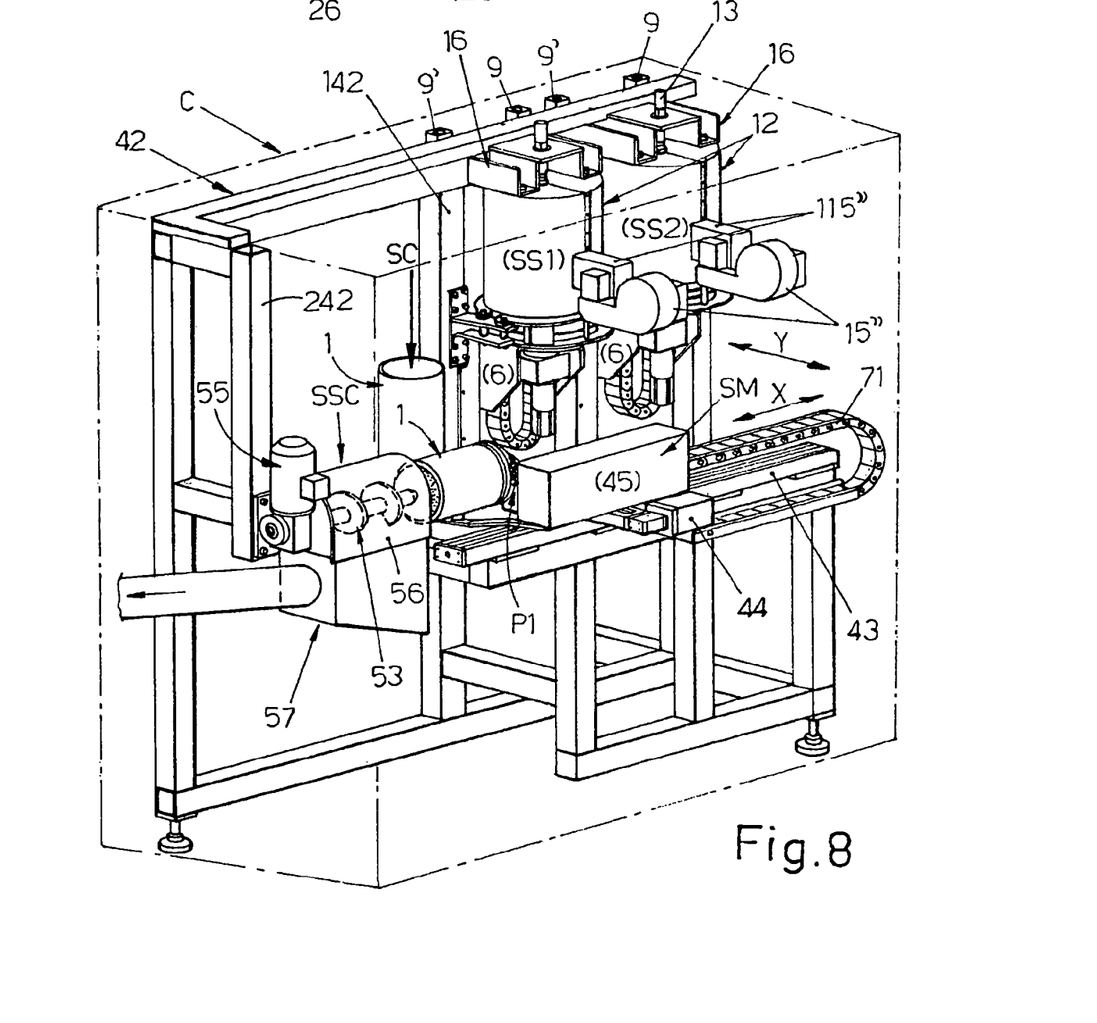
FIG. 8 is a perspective view of a possible form of construction with limited overall dimensions of a machine which comprises a plurality of sterilization stations as shown in the preceding figures, with corresponding service stations.
Figure 9:
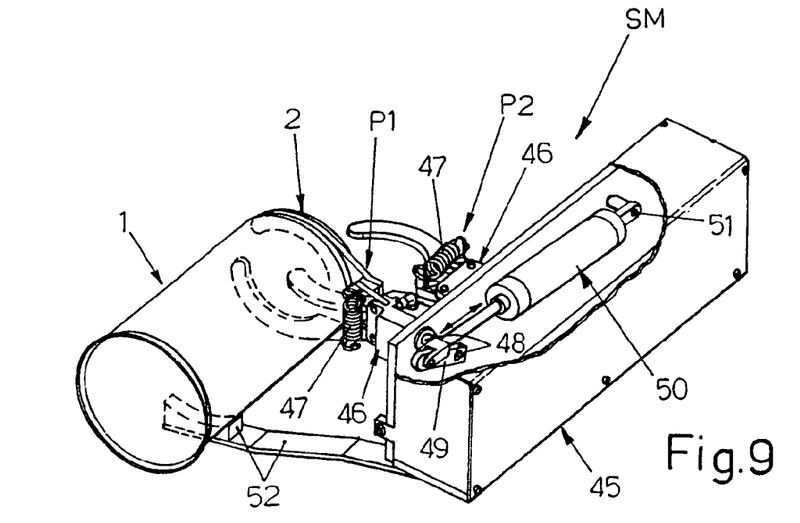
FIG. 9 is a perspective view of the head with two clamps of the station for manipulating the waste canisters, for the transfer of the canisters between the different operating stations of the machine.
Figure 10:
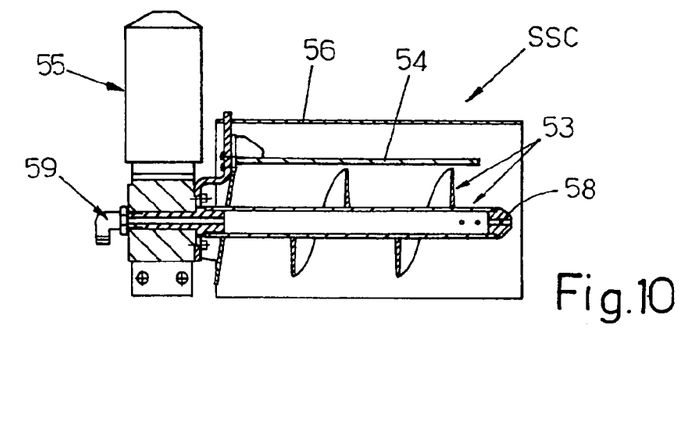
FIG. 10 is a view, with parts in cross section, of the station for the discharge of the waste from one of said canisters.
Figures 11, 12:
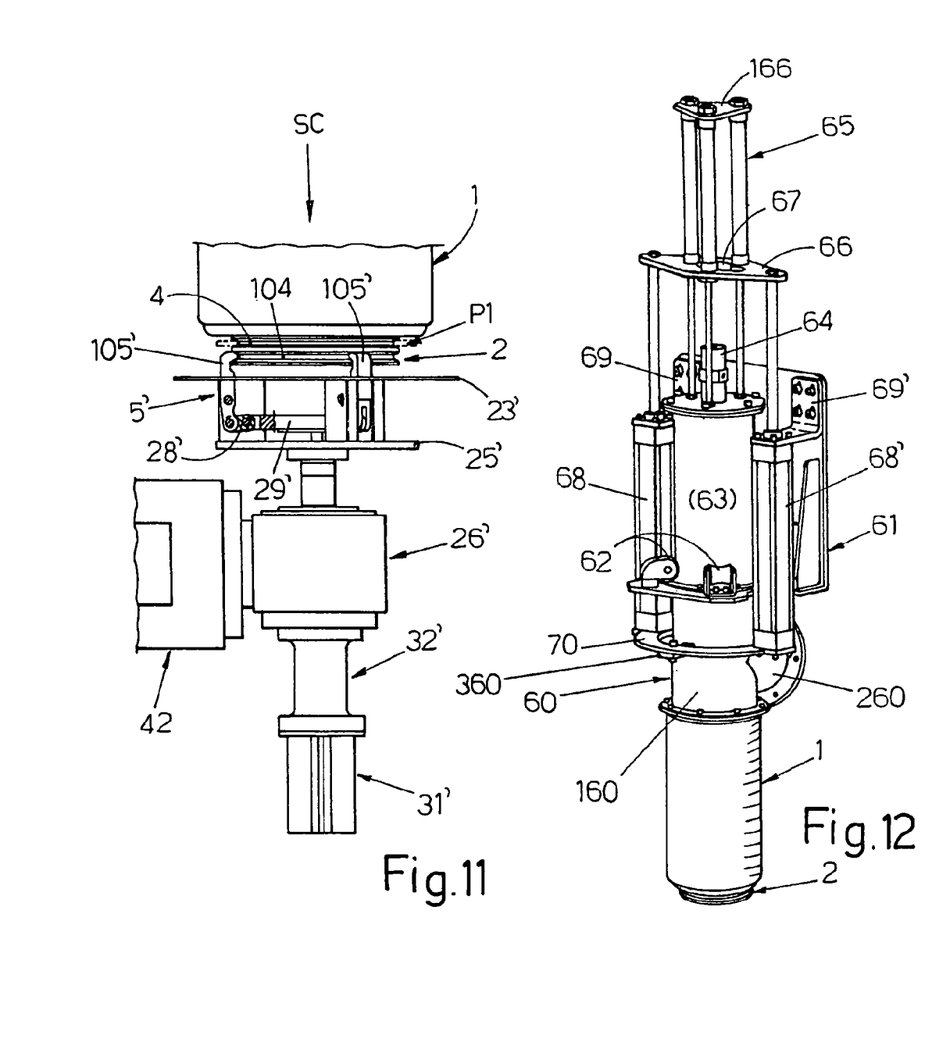
FIG. 11 is a side view, with parts in cross section, of the small rotating platform with a self-centring clamp which supports a canister in the filling station.
FIGS. 12 and 13 are, respectively, a perspective view and a side view, with parts in cross section, of the station for filling with waste a canister supported by the rotating platform of FIG. 11.

Since the operating cycle time of the sterilization chamber 10 is the longest of all the operating times of the various components of a machine provided with sterilization stations of the type described, the invention proposes that the machine be constructed with a layout of the type shown in FIG. 8, by providing two or more sterilization stations SS1, SS2 adjacent to each other on one side of a linear frame 42, and by providing, on the same side, at increasing distances from the first said station SS1, a station SC for filling the canisters 1 with waste and a station SSC for discharging the sterilized waste from the canisters arriving from said stations SS1, SS2. On the same side of the frame 42 as that which carries said operating stations, there are provided suitable automatic means of manipulating the canisters, for transferring the canisters in a closed cycle between the various aforesaid stations. Satisfactory results in terms of reliability and reduced overall dimensions have been achieved by using manipulating means SM operating on at least two orthogonal axes, namely a longitudinal axis indicated by the double arrow X for movement from one station to another, and a transverse axis indicated by the double arrow Y, for movement towards and away from the stations. As shown in FIGS. 8 and 9, said means SM comprise a horizontal guide 43, parallel to the axis X and of suitable length, on which there runs a slider (not shown) carrying an orthogonal guide on which there runs a slider 44 parallel to the axis Y, which supports a head 45 of box-like parallelepipedal shape, with its largest dimension parallel to the guide 43, the wall of the head facing the stations carrying two projecting adjacent self-centring clamps P1 and P2, each having a pair of flat jaws in the form of a sector of a circle, to grip said baseplates 2 of the canisters 1 by the upper grooves 4, these jaws being fixed to the moving elements of actuators 46 of a commercially available type, such as pneumatic actuators, with electrical sensors which detect the open and closed positions of the jaws, which are pushed towards the closed position by corresponding springs 47. The clamp P2 is adapted to perform the opening and closing movement of the corresponding jaws only, and is used for picking up the full canisters from the filling station SC and inserting them into the sterilization stations SS1, SS2, while the clamp P1 is also adapted to open and close and also to rotate about an axis parallel to the axis Y, for example by rotating through ninety degrees, and is used for removing the full canisters 1 from the sterilization stations SS1, SS2 and for inserting them into the discharge station SSC. This object is achieved by mounting the pneumatic actuator which actuates the jaws of the clamp P1 on a shaft 48 (FIG. 9) supported rotatably by means associated with the head 45, this shaft being provided with a crank 49 which is connected to the rod of a cylinder and piston unit 50 whose body is pivoted at 51 on a support inside the head 45. Rotating collectors, which are easily constructed by persons skilled in the art and which are therefore not illustrated, can be provided to enable the supply and discharge line of the actuator 46 and the electrical circuits of the sensors for opening and closing the clamp P1 to pass through the shaft 48. In a simpler alternative solution, said electrical and pneumatic circuits of the clamp P1 can be flexible, can be connected directly to the actuator 46 of the clamp, and can be mounted in a flexible tube which passes through an aperture in the head 45 for connection to the components located inside the head. All the circuits and lines required for the operation of the moving parts of the station SM can be connected to a fixed supply and control panel through circuits and lines located in the track-like conduit 71 shown in FIG. 8. The clamp P1 has its jaws in the horizontal position when it picks up the canister from the self-centring clamp 5 of the rotatable plate 23 of a sterilization station and remains in this position until it reaches the discharge station SSC, where this clamp rotates through 90° to position the canister horizontally as shown in FIG. 9, so that it bears on a support arm 52 fixed to and projecting from the head 45. In this condition, the head 45 moves horizontally along the axis X to insert the canister 1 with the sterilized waste into the station SSC which essentially comprises a horizontal screw 53 having a diameter such that it can enter the canister 1 to be emptied, and an upper longitudinal spear-shaped guide 54 which prevents the rotation of the waste and ensures that it is conveyed and discharged by the screw. The screw 53 has a length which is suitably greater than the height of the canisters 1, and it is mounted on the output shaft of a geared motor 55 fixed to an upright 242 of the frame 42 of the machine (FIG. 8). The screw assembly 53, 54 is protected, with sufficient clearance, by a casing 56 which is open downwardly and to the bottom of which suitable means 57 are connected for collecting the discharged waste or carrying it to a remote location (FIG. 8). FIG. 10 shows that the shaft of the screw 53 is axially hollow and is provided with a tip with nozzles 58 for discharging at least one pressurized fluid, such as air and/or water, which is supplied to this shaft through a rotating joint 59, to ensure that the canister 1 is sufficiently cleaned internally before being removed from the station SSC and being reinserted in a new operating cycle. On completion of the discharge and cleaning, the head 45 is retracted horizontally to withdraw the canister from the screw 53, and, when the retraction has been completed, the clamp P1 rotates through ninety degrees to return the canister to the vertical position with its mouth upwards, and in this condition the canister is aligned and inserted by the manipulator SM into the discharge station SC which has means for supporting the canister and which will be described below with reference to FIGS. 11 to 13. FIGS. 8 and 11 show in greater detail how the canister 1 which has been emptied in the discharge station SSC is held by the lower groove 4 by the clamp P1 and is positioned horizontally, and, following a translational movement of the head 45 along the axis Y, is positioned by this head above the open jaws 105' of a self-centring clamp 5' which is similar to the clamp 5 present at the sterilization stations SS1, SS2, but which, unlike the latter clamp, is provided solely for the purpose of rotation and not for the purpose of providing raising and lowering movements, and is positioned in the lower part of the filling station SC. The lower plate 25' is fixed to the output shaft of a geared motor 26' which is fixed by its casing to the frame 42 of the machine and which, as in the arrangement shown in FIG. 4, is provided in its lower part with the cylinder and piston unit 31' and the freewheel device 32' for the actuation of the operating plate 29' which by means of the links 28' transmits the necessary oscillation to the jaws 105' for their opening and closing movements. Before a canister is inserted into the discharge station SC, the clamp P2 removes a canister full of waste from this station, after which the head 45 translates the full canister and inserts it into whichever of the sterilization stations SS1 or SS2 is available, after the canister full of sterilized waste has been removed by the clamp 5 of the station, in such a way that, while one canister is being filled in the station SC, the head 45 carries out the aforesaid operations and then returns with the full canister to the discharge station SSC for the start of a new operating cycle.

Figure 13:
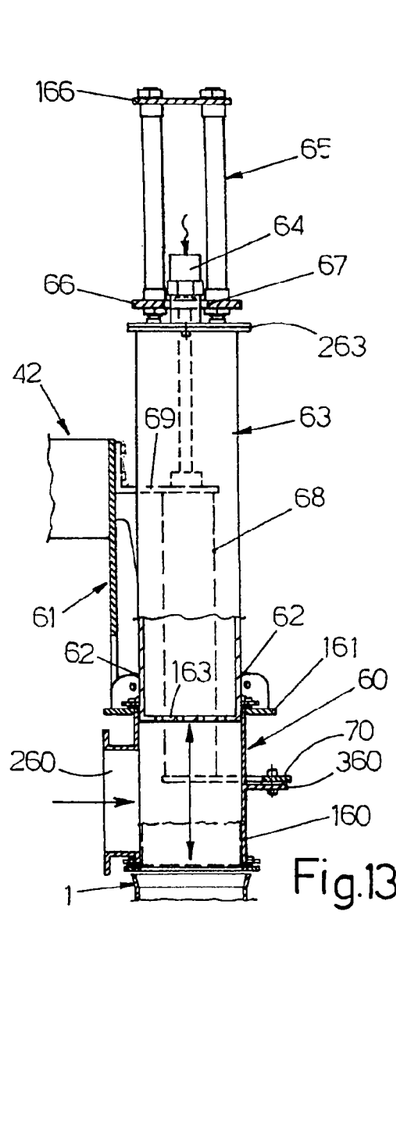

As shown in FIGS. 12 and 13, the filling station SC comprises a T-shaped tubular pipe 60, the canister 1 to be filled being placed under the vertical branch 160 of this pipe and in axial alignment with it, while the horizontal branch 260 of the pipe is connected to any suitable means of supplying the waste to be sterilized, after the waste has been suitably shredded by known means. The upper end of the vertical branch of the pipe 60 is flanged to a collar 161 placed at the base of a strong bracket 61 fixed to a component of the frame 42 of the machine, and the collar 161 also carries rollers 62 with horizontal axes and curved generatrices which axially guide the lower portion of a hollow cylindrical piston 63 which is slidable in the underlying pipe branch 160 and which has a suitably perforated base wall 163 and a closed upper end 263, the piston carrying axially a pipe 64 connected to a circuit which is activated on command to introduce appropriate quantities of water to moisten the waste loaded into the canister 1 (see below). The piston 63 has an outside diameter such that it can enter the canister 1 with sufficient clearance in the filling phase and has a length suitable for the purposes described below. The head 263 of the piston 63 is connected, at points spaced at equal angular intervals, to the rod of three vertical double-acting hydraulic cylinder and piston units 65, which are fixed by the lower and upper ends of their bodies to cross-pieces 66 and 166 respectively. The lower cross piece 66 has a central aperture 67 to prevent interference with the pipe 64 and is lozenge-shaped in plan view, with its longer dimension parallel to the vertical plane containing the bracket 61, and the ends of the cross piece 66 are connected to the rod of corresponding vertical double-acting hydraulic cylinder and piston units 68, 68', the ends of whose bodies are fixed, respectively, to upper brackets 69, 69', fixed to the bracket 61 and to a lower cross piece 70 in the form of a sector of a circle, the intermediate part of which is fixed to an appendage 360 of the pipe 60. When the canister 1 is being filled with waste, the cylinder and piston units 65 are in the retracted position as shown in FIG. 13, causing the piston 63 to be positioned with its base above the horizontal branch 260 of the pipe 60, so that the waste arriving from this branch has to flow downwards and into the canister 1 which is made to rotate slowly about its own axis by the rotating clamp 5' of FIG. 11. In the operating cycle of the filling station SC, according to a specified procedure in terms of timing and/or in accordance with the operation of means which detect the flow of waste through the pipe 60, the rotation of the canister 1 ceases after the waste placed in it has been uniformly distributed, the supply of the waste is halted, and the piston 63 is lowered to the low position shown in broken lines in FIG. 13 and as shown in FIG. 12, as a result of the extension of the rods of the upper cylinder and piston units 65. In the next step, the rods of the lower cylinders 68, 68' are retracted to push the piston 63 into the canister, thus ensuring the appropriate compaction of the waste in the canister, and a suitable quantity of water is then poured onto the waste through the upper pipe 64 and through the piston which is perforated at its base. Suitable means (not shown) can also be provided on the lower filling aperture of the branch 160 of the pipe 60 so that a suitable quantity of liquid can also be added to the waste during the intermediate steps of the cycle of filling the canister 1. The compression of the waste can be monitored by means of a proportional valve, pressure gauges, load cells and/or other suitable means. On completion of the compaction and moistening, the various components of the station SC return to the initial position of FIG. 13. This operating cycle can be carried out either once only (at the end) or a number of times during the filling of a canister 1, and the filling cycle ceases when suitable means detect that the canister is full in terms of volume, for example by detecting the travel of the rods of the pistons 68, 68', by means of any suitable linear movement transducers such as magnetic sensors which detect the positions of the pistons of the cylinders 68, 68', linear encoders, or the like (not shown).

The machine as shown in FIG. 8 occupies a space which is limited in both width and length, and can be assembled and wired ready for use inside a freight container C of standard dimensions provided with doors at the opposite ends for access by maintenance personnel, mainly at the end where the sterilization stations SS1, SS2 are located, and for the operations of filling and discharge of the waste by the discharge station SSC. The means for conveying the containers of infected waste can be located behind the frame 42, these containers being discharged by an automatic manipulator into a shredder which is also located in the freight container and which is served by a discharge conveyor leading to the pipe 60 of the aforesaid station SC. If the waste container is of the disposable type, it is placed in the shredder together with the waste contained in it. However, if the waste container is of the recoverable type, it is emptied and can be inserted, in the inverted position, into a cleaning station which may incorporate rotating brushes, and is then placed on a conveyor for removal. The freight container C can be connected to suitable means for extracting air from inside it and means for treating and sanitizing the extracted air before its discharge into the atmosphere, to prevent any dispersion of contaminants into the environment. These means have not been illustrated in the drawings, since they can be of the type described in the preceding patent application cited in the introduction to the present description, or can be of any suitable type.

The invention claimed is:
1. A machine for neutralizing the bacterial content of hospital waste or other special waste, so as to be able to dispose of such waste similar to ordinary solid waste, in which the waste to be sterilized, having been shredded and moistened, is placed in a microwave-permeable cylindrical canister which is placed in a sterilization chamber, each canister being cylin- drical in shape and having an open top and which has a baseplate on its bottom with an upper annular groove and a lower annular groove, and wherein the machine includes a frame, at least two sterilization stations, each having a sterilization chamber, the chambers being positioned side by side on the frame, the machine comprising the following:

(a) a plurality of sterilization stations, each sterilization station comprising:

a sterilization chamber made of a wholly or partially microwave-opaque material and provided with waveguides, wherein each of the waveguides is connected to a corresponding magnetron to transmit microwave radiation to the interior of the sterilization chamber a structure which rotates a canister, when in a sterilization chamber to ensure that the radiation from the waveguides is distributed to the whole mass of the waste in the canister, the sterilization chamber having the shape of a cylinder with its bottom opened downwardly, and including a structure which can seal off the lower opening;

(b) a raising and lowering mechanism at each sterilization station which is constructed to raise a canister with its axis positioned vertically into the chamber, and after sterilization, to lower that canister out of the chamber;

(c) a transfer mechanism which is operable when a canister is not in a sterilization chamber to rotate that canister from a vertical axis position to a horizontal axis position to move that canister linearly along its axis when it is in its horizontal axis position, and to move that canister horizontally, while in its vertical axis position;

(d) a filling station mounted on the frame and located adjacent to the sterilization stations and arranged to fill a canister with waste to be sterilized, while the canister is in a vertical axis position;

(e) a discharge station mounted on the frame and located adjacent to the filling station and arranged to receive sterilized waste from a sterilized canister while that canister is in its horizontal axis position;

(f) the transfer mechanism arranged to move a canister between a sterilization station, the filling station and the discharge station, including positioning that canister in the correct horizontal axis or vertical axis position at each of the respective stations, said transfer mechanism further comprising a head which is moveable along at least two orthogonal axes, namely a longitudinal axis for moving a canister from one station to another and a transverse axis for a canister moving towards and away from the stations, said head carrying first and second projecting self-centering clamps which face the stations and are adjacent to each other, each clamp having a pair of jaws in the form of sectors of a circle, to grip the baseplate of each canister by the upper groove, the first of said clamps performing only the movement of opening and its jaws and being used to remove a full canister from the filling station and inserting it into a sterilization chamber of a sterilization station, while the second clamp rotates through ninety degrees about an axis parallel to said transverse axis for moving a full canister from a sterilization station and for inserting it into the discharge station, and wherein when the head with the first clamp carrying a full canister which has been collected from one of the sterilization stations reaches the discharge station, the first clamp rotates through ninety degrees to position the canister horizontally so as to bear on a support arm fixed to and projecting from the head, which head moves horizontally along the axis of the cylinder to insert the canister of sterilized waste into the discharge station, and wherein the discharge station comprising a horizontal screw, the length of which is greater than the height of a canister and movable by a geared motor and having a diameter such that it can enter the canister to be emptied, and including at least one longitudinal spear-shaped guide which prevents the rotation of the waste within the canister and ensures that the waste is conveyed and discharged by said screw into a collector which collects and carries away the discharged waste, the shaft of the screw being axially hollow and provided on its free end with a tip having nozzles for the discharge of pressurized fluid supplied to the shaft through a rotary joint to ensure that that canister is sufficiently cleaned before or during movement away from the discharge station.

2. A machine according to claim 1, wherein each canister has a flared upper aperture forming the open top and includes on its bottom a base having an axial shank which has an anti-slip outer profile which has fixed thereto said baseplate comprising two parts which are fixed together and to said shank, the baseplate being mushroom shaped with a head bearing against the base of the canister and with a stem in which are formed said upper and lower grooves, the upper groove designed to be gripped by a transfer mechanism and the lower groove designed to be gripped by structure which rotates the canister.

3. A machine according to claim 1, wherein each sterilization chamber includes a lower flange having a stepped inner profile into which can be fitted a flange with a complementary profile with seals located therebetween, the flange being fixed on the upper edge of a cylindrical sleeve which is in turn fixed with a seal to a carriage mounted on a guide and slider mechanism provided for raising and lowering the carriage, a geared motor mounted under the carriage and having a shaft extending upwardly therefrom into a sleeve at which it supports a lower plate and an upper plate, the upper plate being located at the height of the said flange and being fixed to the lower plate by spacers, pivoted jaws being mounted on one of the spacers and having a self-centering clamp which passes through apertures in the upper plate and is connected by links to an operating plate associated with a raising and lowering rod which passes axially through the output shaft of the geared motor and then projects from the outer part of the shaft for connection to a rectilinear raising and lowering actuator, with the interposition of a freewheel device.

4. A machine according to claim 3, wherein each sterilization chamber is formed by a tubular sleeve made of a microwave-permeable material enclosed externally by a shield, each chamber being sealed at its top by a lid and being sealed at its open bottom against the flange and secured to the lid by rods, a casing located above the lid spaced therefrom by spacers and screwed to the lid, the casing and the outer lateral surface of each chamber of the casing being constructed to provide additional shieldings for microwaves, support screws of the spacers having a length such that they project from the casing and are fixed by bolts to composite supports which are in turn fixed to the frame of the machine.

5. A machine according to claim 3, including a collar clamp enclosing the flange of each sterilization chamber and having jaws which are supported by supports which are fixed to the frame of the machine, including an actuator for opening and closing the jaws and which supports rocker arm supports, and including blocks, each in the form of a sector of a circle in plan view, having an inwardly facing groove with a profile in the form of an isosceles trapezium having inclined planes, the inclined planes interacting with the upper edge of the lower flange of each chamber and with the lower edge of the movable flange which seals the bottom of each chamber and which is associated with the raising and lowering structure while the clamp supports and rotates a canister, wherein the flanges are maintained and sealed in opposition to the high pressure developed in each chamber.

6. A machine according to claim 1, wherein after the canister has been emptied at the discharge station and brought to a vertical position by said second clamp, it is positioned by longitudinal movement of the head above opened jaws of a said second clamp, the filling station comprising a T-shaped tubular pipe under a vertical branch of which there is placed, a short distance away and in axial alignment, the aperture of a canister to be filled, while a horizontal branch of the T is connected to a supply of waste to be sterilized, the upper end of the vertical branch of the pipe being flanged to a collar located at the base of a bracket which is fixed to the frame of the machine, and including rollers on the collar to axial guide the lower portion of a hollow cylinder piston which slides in the vertical branch of the pipe, the piston having a perforated base wall and a closed upper end which carries an axial pipe connected to a circuit which is activated on command for the introduction of water for moistening the waste loaded into the canisters, the piston being connected to axial movement actuators which, during the filling of the canisters maintain the lower end of the piston above the horizontal branch for the entry of the waste, and which, on command, causes the piston to descend into the canister to compress the waste loaded into the canister and to moisten the waste inside of the canister, this operating cycle of the lower end of the piston being carried out during the filling of a canister, and wherein the filling cycle ceases when filling of the canister is completed.

7. A machine according to claim 1, wherein the machine occupies a space which is defined by a given width and a given length such that it can fit within a freight container with at least such width and length and having doors at opposite ends for access by maintenance personnel and for the operations of filling and discharge of waste at the filling and discharge stations, said container being dischargeable into a shredder which is also located in the freight container which is served by a discharge conveyor leading to the inlet of the filling station, a canister being placed in the shredder together with the waste which it contains.

* * * * *